(12) United States Patent
Hamblen et al.

(10) Patent No.: US 6,604,432 B1
(45) Date of Patent: Aug. 12, 2003

(54) SOIL COMPACTION MEASUREMENT

(75) Inventors: William R. Hamblen, Stow, MA (US); Frank Berkman, Newton Centre, MA (US); Bill Watters, Gloucester, MA (US)

(73) Assignee: BBN Corporation, Cambridge, MA (US)

( * ) Notice: Subject to any disclaimer, the term of this patent is extended or adjusted under 35 U.S.C. 154(b) by 0 days.

(21) Appl. No.: 09/530,662

(22) PCT Filed: Jan. 23, 1997

(86) PCT No.: PCT/US97/00990

§ 371 (c)(1),
(2), (4) Date: May 2, 2000

(87) PCT Pub. No.: WO97/28432

PCT Pub. Date: Aug. 7, 1997

Related U.S. Application Data

(63) Continuation-in-part of application No. 08/595,256, filed on Feb. 1, 1996.

(51) Int. Cl.[7] .................................................. G01L 1/00
(52) U.S. Cl. ................................................ 73/784; 73/594
(58) Field of Search ............................ 73/594, 579, 584, 73/784, 794, 84

(56) References Cited

U.S. PATENT DOCUMENTS

| | | | |
|---|---|---|---|
| 1,871,756 A | 8/1932 | Spath | 73/594 |
| 3,224,253 A | 12/1965 | McKay | 73/594 |
| 3,362,216 A | 1/1968 | Hardin et al. | 73/594 |
| 3,427,877 A | 2/1969 | Swift et al. | 73/146 |
| 3,481,183 A | 12/1969 | Swift | 73/573 |
| 3,643,498 A | 2/1972 | Hardin | 73/594 |
| RE27,875 E | 1/1974 | Swift | 73/67.1 |
| 3,795,286 A | 3/1974 | Meyer | 73/594 |
| 3,813,929 A | * 6/1974 | Hardin et al. | 73/784 |
| 3,863,202 A | 1/1975 | Landrum, Jr. | 73/594 |
| 3,924,451 A | * 12/1975 | Drnevich | 73/594 |
| 3,946,598 A | 3/1976 | Towne et al. | 73/594 |
| 4,127,351 A | 11/1978 | Vural | 404/72 |
| 4,149,253 A | 4/1979 | Paar et al. | 404/84 |
| 4,348,901 A | 9/1982 | Vural et al. | 73/594 |
| 4,382,384 A | 5/1983 | Mitchell et al. | 73/594 |
| 4,445,378 A | 5/1984 | Zuckerwar | 73/594 |
| 4,467,652 A | 8/1984 | Thurner AB et al. | |
| 4,594,899 A | 6/1986 | Henke et al. | 73/784 |
| 4,655,082 A | 4/1987 | Peterson | 73/594 |
| 4,738,138 A | 4/1988 | Redman-White | 73/594 |
| 4,750,157 A | 6/1988 | Shei | 73/594 |
| 4,912,979 A | 4/1990 | Sondergeld et al. | 73/594 |
| 4,918,988 A | 4/1990 | Ebihara et al. | 73/594 |
| 4,995,008 A | 2/1991 | Hornbostel et al. | 73/594 |
| 5,105,650 A | 4/1992 | Atkinson et al. | 73/594 |
| 5,398,215 A | * 3/1995 | Sinha et al. | 367/31 |

* cited by examiner

Primary Examiner—Richard A. Moller
(74) Attorney, Agent, or Firm—Leonard Charles Suchyta; James K. Weixel (57) ABSTRACT

The in-situ measurement of the shear modulus of a surface layer of soil (12) is performed by apparatus in which a contact foot (11) with a preselected downward bias force engages a defined area of a region of soil. A drive transducer (13) shakes the contact foot (11) vertically and sensing transducers (17, 18) determine the force applied to the foot (11) and the resulting movement of the foot (11) and generate respective first and second output signals. The in-phase movement responsive output signal is analyzed in relation to the force signal to obtain a measurement of a single parameter which is representative of the stiffness provided by the soil (12). The shear modulus as well as the void ratio of the soil can be calculated from the stiffness. The drive transducer (13) is energized by an a.c. signal which progressively varies in frequency over a preselected band with the rate of change also varying with frequency thereby providing a greater force spectrum content at lower frequencies than at higher frequencies in the band, while maintaining a substantially constant force magnitude.

21 Claims, 7 Drawing Sheets

SOIL COMPACTION MEASUREMENT

CROSS-REFERENCE TO RELATED APPLICATION

This application is a section 371 National Stage Application of international application No. PCT/US97/00990, filed Jan. 23, 1997 and published as WO97/28432, in English which is a continuation in part of and claims priority from U.S. Application No. 08/595,256, filed Feb. 1, 1996.

BACKGROUND OF THE INVENTION

The present invention relates to the measurement of the properties of soil and more particularly to apparatus for measuring the shear modulus of soil to determine the extent of compaction.

As is understood, soil is an important building material. It serves as the base for virtually all pavements, tunnels and buildings, and thus, can be thought of as an element used in construction. In construction, soil will typically be specified to have certain minimal mechanical properties, e.g., dry density, resilient modulus and strength. While some testing can be conducted in a laboratory, e.g., to determine the suitability of a raw material or blend of materials, it is also typical to perform field tests to monitor both the soil selection or composition and also the compaction which affects mechanical properties of interest, typically a specified void ratio or resilient modulus.

The present field test procedures are typically sand cone or nuclear densitometric measurements. The sand cone requires substantial elapsed time while the nuclear densitometric measurement is often not considered sufficiently reliable and also raises radiation concerns. Accordingly, there exists a need for an ability to do rapid, low cost field tests which will reliably indicate the mechanical properties of the soil. As is understood by those skilled in the art, soil used to fill or level a construction site must be compacted, typically by the application of vibratory energy and weight, in order to obtain the requisite density and modulus. Typically, contractors are forced to over-compact soil as each of successive layers are added in order to insure that the result will meet the requisite specification when completed. The ability to quickly and reliably test soil properties could significantly reduce costs by eliminating the practice of over-compacting so as to provide a large margin over the specification.

While it has previously been proposed to measure soil properties by dynamic impedance measurements, no such prior system has found acceptance since the readings have been found to be inconsistent and not generally repeatable.

Among the several objects of the present invention may be noted the provision of novel apparatus for the insitu measurement of soil properties; the provision of such apparatus which will allow accurate measurement of the shear modulus of a surface layer of soil; the provision of such apparatus which provides accurate and repeatable measurements; the provision of such apparatus which will provide measurements reliably indicative of the state of compaction of soil; the provision of such apparatus which may be easily and quickly operated; the provision of such apparatus which can be easily transported to a construction site and easily moved between successive measurement positions at the site; the provision of such apparatus which is highly reliable and is of relatively simple and inexpensive construction. Other objects and features will be in part apparent and in part pointed out hereinafter.

SUMMARY OF THE INVENTION

The apparatus of the present invention is adapted for the in-situ measurement of the shear modulus of soil and employs a contact foot for engaging a defined area of a region of soil to be measured. A pre-selectable downward bias force is applied to the contact foot which is designed to minimize variability in the foot's coupling to soil surfaces which typically are not perfectly flat, uniform, or which lack cohesion. A drive transducer is provided for shaking the contact foot vertically in response to drive signals applied thereto, preferably through a calibrated spring. Sensing transducers detect the force applied to the foot and the movement or acceleration of the foot and generate corresponding first and second output signals. The drive transducer is preferably driven by an a.c. drive signal which progressively varies in frequency over a pre-selected band with the rate of change also varying with frequency so that, for constant force amplitude, the force spectral content is greater at frequencies which would otherwise have a poorer signal-to-noise ratio, typically the lower frequencies. The in-phase component of the second output signal is analyzed in relation to the first output signal to obtain a measurement which is representative of the shear modulus.

BRIEF DESCRIPTION OF THE DRAWINGS

Corresponding reference characters indicate corresponding parts throughout the several views of the drawings.

DESCRIPTION OF THE PREFERRED EMBODIMENTS

Figure 1:
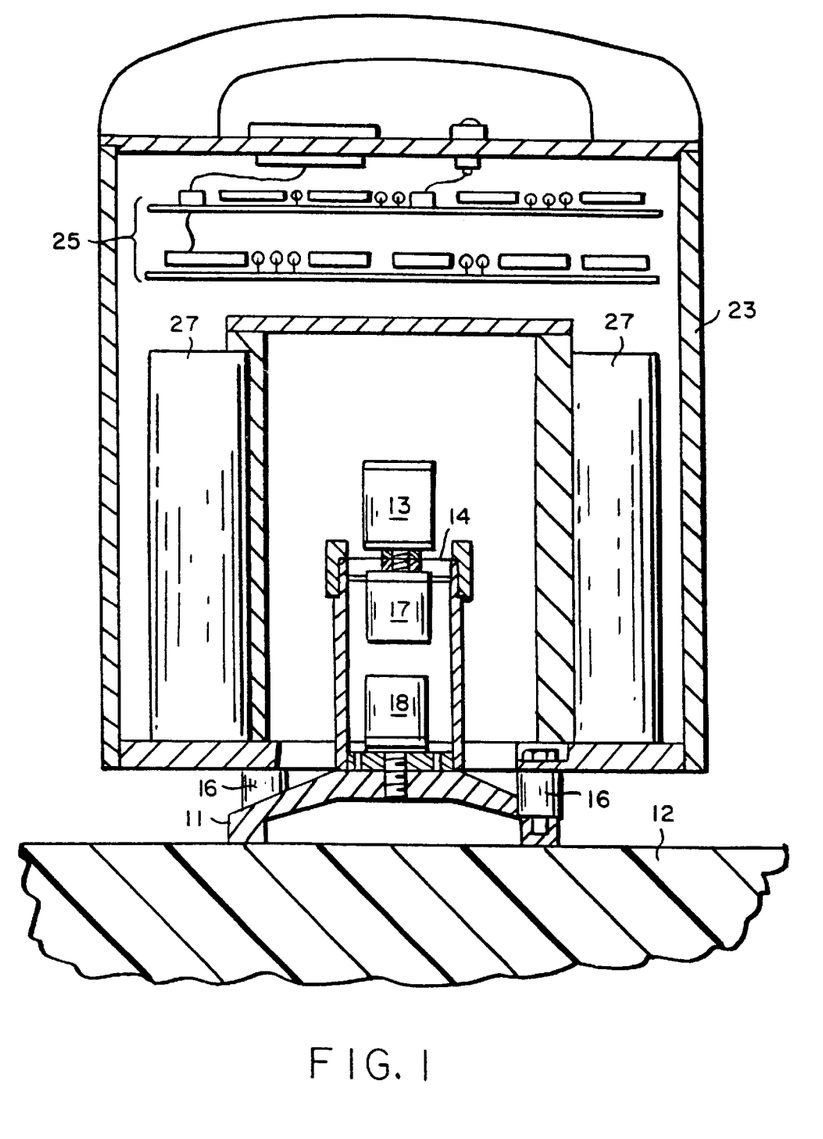
FIG. 1 is a side view of measurement apparatus in accordance with one embodiment of the present invention.

Referring now to FIG. 1, the apparatus illustrated there is intended to be man portable, i.e., so that a worker can easily move it from location to location within a construction site. The apparatus is designed to stand on a contact foot 11 which, as is described in greater detail hereinafter, engages a defined surface area or region of soil 12 to be tested. The nominal diameter of the foot corresponds or is roughly proportional to the depth of the surface layer to be tested. In the preferred embodiment illustrated, the diameter of the foot is about 4½ inches. This has been found appropriate for fill layers up to about 12 inches. In a man portable instrument as contemplated by the present invention, foot diameters up to 12 inches may be considered appropriate. Likewise, while a circular foot is preferred, it should be understood that somewhat non-circular contact foot members might also be used.

A drive transducer, e.g., in the form of a electromechanical linear motor 13, is provided for shaking the contact foot vertically in response to drive signals applied to the transducer. The motor 13 is not connected directly to the foot 11 but rather is connected through a disk shaped calibrated spring 14 and a cylindrical coupling 15. The output element of motor 13 is connected to the center of the spring 14. When the motor is energized with an a.c. signal, the output element oscillates the center of the spring, working against the inertial mass of the motor itself. While the spring 14 is circular, it is convenient in terms of force analysis and claim wording to refer to the center of the spring as its input "end" and the periphery of the spring as its output "end", since other forms of calibrated spring could be used.

A first geophone 17 senses the motion applied to the spring 14 while a second geophone 18 senses the resulting motion of the foot 11 which contacts the soil 12. Since the compliance of the spring 14 is predetermined and known, the force applied to the foot can be calculated from the difference in the velocities measured by the two geophones 17 and 18. As is understood by those skilled in the art, the geophones 17 and 18 are moving coil velocity sensors which provide an output voltage proportional to velocity. The motor 13 can be constituted by a larger geophone with the exitation being applied to the moving coil output element which is connected to the center of spring 14.

Mounted on the foot 11 via a set of resilient rubber isolation mounts 16 is a housing 23 which carries an electronics package 25 and a series of batteries 27 distributed circumferentially around the axis of the motor 13. The batteries 27 will typically constitute a substantial portion of the weight needed to provide a predetermined downward static bias on the contact foot 11. A handle 28 is provided for moving the instrument. In the preferred embodiment illustrated, the total weight providing a steady downward bias on the foot 11 is about 35 lbs. As will be understood, the appropriate bias weight will be roughly proportional to the area of soil surface contacted by the foot.

Figure 2:
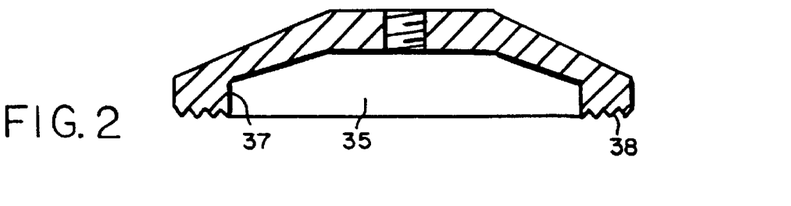
FIG. 2 is a cross-sectional illustration of a contact foot utilized in the apparatus of FIG. 1.

Referring now to FIG. 2, the foot 11 provides a slightly arched or domed central portion 35 and a downwardly projecting annular rim 37 which acts to control the pattern of stress on the soil to the desired distribution. The foot is preferably constructed of a light weight material such as aluminum since the mass of the foot must be effectively subtracted in making the impedance measurement as described hereinafter. Preferably, the bottom surface 38 of the annular rim 37 is roughened; e.g., by very coarse sand paper.

Figure 2A:
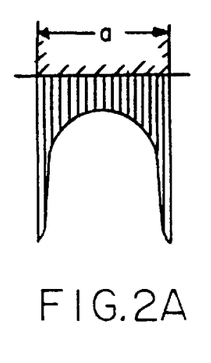
FIGS. 2A–2C is a figure taken from Civil Engineering literature illustrating the expected variability in distribution of the pressure on the base of a rigid circular foot. This variability in distribution can lead to variability in the measured stiffness. The annular contact area of the foot of FIG. 2 and of FIG. 4 was chosen to minimize this variability.
Figure 2B:
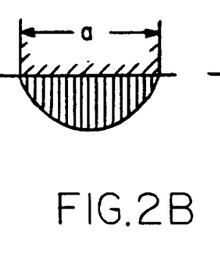
Figure 2C:
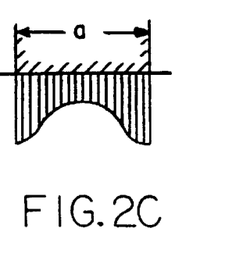

FIGS. 2A, 2B and 2C are taken from Karl Terzaghi and Ralph B. Peck, *Soil Mechanics in Engineering Practice*, John Wiley and Sons, 1967 and represent the distribution of contact pressure on the base of a smooth rigid footing supported by (a) real, elastic material; (b) cohesionless sand; (c) soil having intermediate characteristics, respectively. These figures illustrate the motivation for the design of the annular contact area of the foot of FIG. 2. The drastic change in pressure distribution FIGS. 2A and 2B is believed to be due to slippage between the foot's lower surface and the soil. The annular design of FIG. 2 limits the pressure distribution to an approximation of that in FIG. 2A, a preferred distribution. The rough surface shown on the bottom surface 38 of the annular rim of FIG. 2 is provided to further limit the slippage mechanism.

Figure 3:
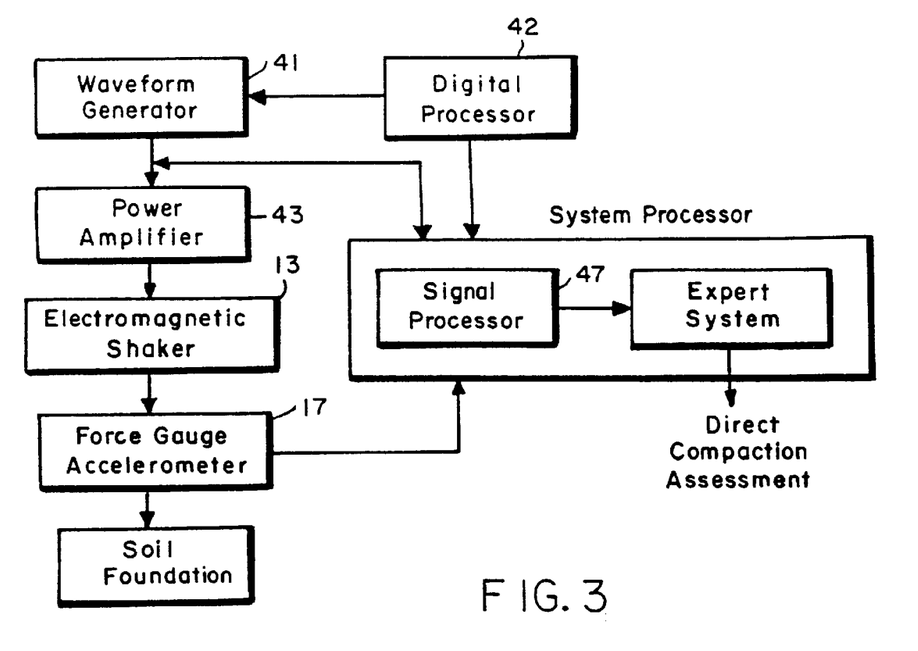
FIG. 3 is a block diagram of drive, sensing and analysis electronics employed in the apparatus of FIG. 1.

Referring now to FIG. 3, the electronic system illustrated there includes a programmable waveform generator 41. The operation of the waveform generator 41 is preferably initiated and controlled by a programmable digital processor 42. A digital signal processor 47 receives the signals generated by the geophones 17 and 18 and also the signal generated by the waveform generator 41. The displacement of the foot 11 is obtained by a single integration of the signal from geophone 18. The force is obtained from the difference of the two geophone signals (after single integration), and the known spring constant. In effect, the desired value of the complex mechanical impedance of the soil (seen through the contact with the foot) is obtained by comparison with the known mechanical impedance of the calibrated spring.

Under the control of processor 42, the waveform generator 41 generates an a.c. signal which progressively varies in frequency over a preselected band; e.g., 50 to 150 Hz, with a rate of change of frequency which also varies with frequency so that, for constant amplitude, energy content is greater at some frequencies; e.g., at lower frequencies than at higher frequencies. This progression is advantageous in improving signal to noise ratio as described in greater detail hereinafter. The signal provided by the waveform generator 41 is applied, through a power amplifier 43 to the motor or drive transducer 13. The real component of the displacement signal; i.e., the component which is in-phase with the force applied to the contact foot is then extracted from the complex signal; i.e., the signal comprising both real and imaginary parts.

It has been found that extracting the real component improves the accuracy of the measurement of the shear modulus, as compared with using the absolute amplitude of the displacement signal, since the quadrature component arises largely due to various lossy mechanisms in the complex behavior of soil. Likewise, while measurement at a single frequency would theoretically be possible, the actual behavior of soil has been found to be somewhat frequency dependent.

Frequency-dependent behavior or resonances may be caused by (a) standing seismic waves caused by reflections from the sides of a road bed or from the sides of a trench where the soil is being compacted; or (b) improper contact between the soil and the measurement foot. Such resonance effects can be removed by averaging the measured data over a wide frequency range, or else by deleting a narrow band of anomalous data from the average.

Given the use of a substantial band of measuring frequencies, the signal-to-noise ratio and the resulting final accuracy can be improved if tracking filters are incorporated into the signal processor. Since measurements are made at one frequency at a time, tracking filters can be used to reject noise in the force and displacement signals at all other frequencies.

One technique for implementing such filters is to use FFT processing, stepping the test frequency from one bin to another bin. Another technique is to utilize synchronous detection, making use of a quadrature (i.e. sine and cosine) oscillator to obtain the desired complex ratio of force to displacement. An advantage of the synchronous detector approach is that much of the signal processing can be done utilizing analog computer techniques, substantially reducing the cost of the analog/digital signal processor.

Another advantage of using a substantial range of frequencies is that interference from tonal noise can be more easily excluded from the final determination, either by operator decision to exclude atypical frequency components, or by an automatic expert system as indicated at reference character 48. An example of a tonal source of interfering noise would be a vibrating soil compactor operating in the general vicinity in which the test measurements are taking place.

Figure 8:
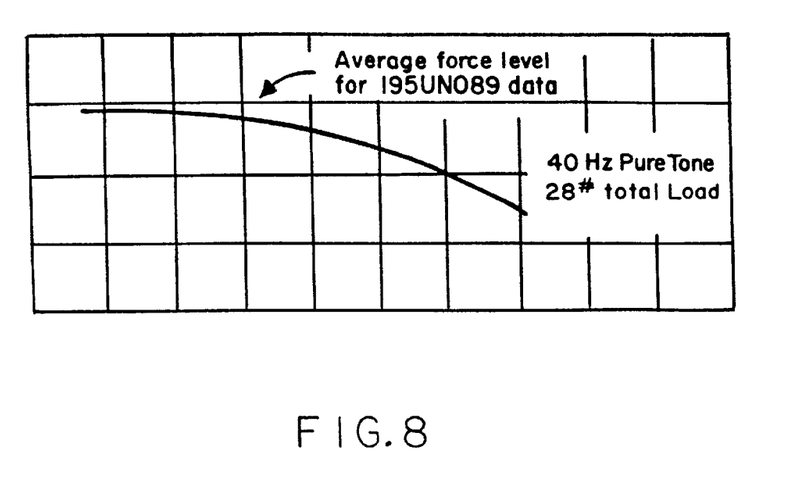
FIG. 8 is a plot of the measured stiffness of compacted soil, showing the measurement error which can result from using excessively large dynamic force levels.

In order to provide an accurate measurement, the amplitude of the excitation force applied to the shaker motor 13 must be limited to a fairly low level. Otherwise, the measurement process itself can introduce compacting effects or may interfere with the measurement process by causing slippage between adjacent grains of the soil material so that the resultant measurement does not accurately reflect static shear modulus. This effect is illustrated in FIG. 8, where the measured average stiffness of well-compacted "processed gravel" (as might be used as the sub-grade for a highway) is plotted, for a range of dynamic force test levels. Clearly, the poor signal-to-noise ratio which might exist at a test site where road construction work is in progress cannot be corrected by simply increasing the test force level.

Figure 9:
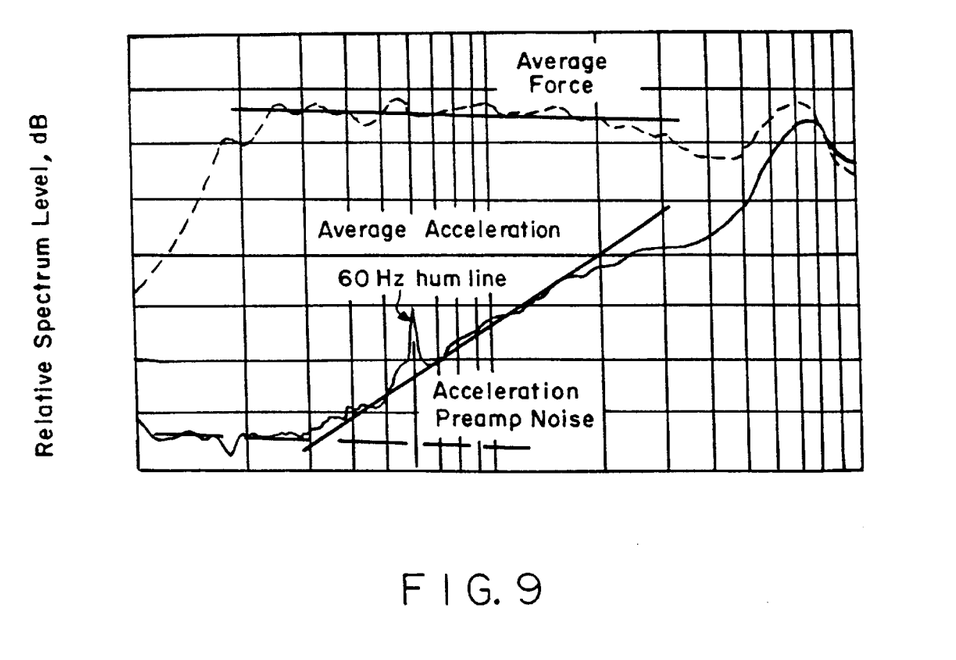
FIG. 9 is a plot of the force spectrum level applied to compacted soil during a field test of its shear modulus, as well as the acceleration spectrum level resulting from the applied force.
Figure 10:
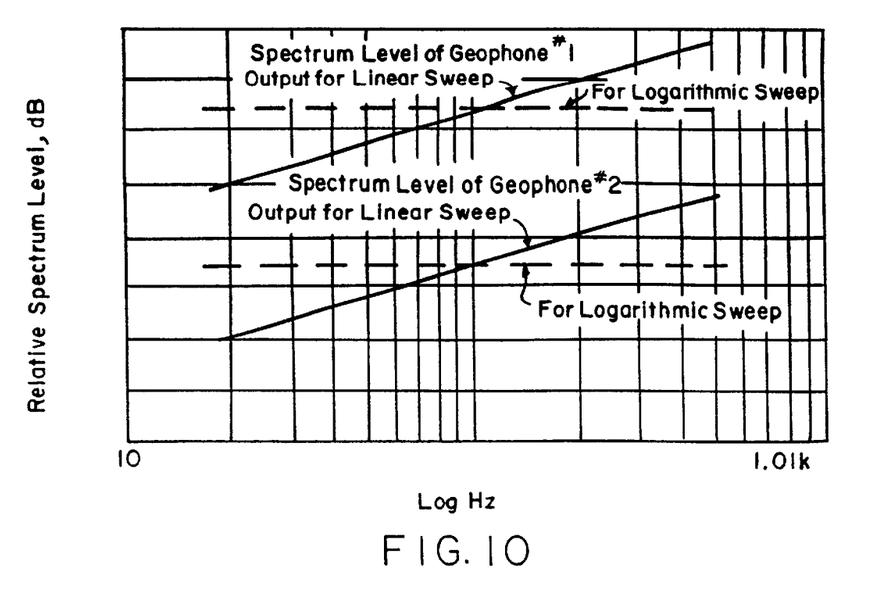
FIG. 10 illustrates the advantage of replacing the accelerometer used for FIG. 9 with a geophone as used in FIG. 1, and the further advantage of using a nonlinear frequency sweep.

FIGS. 9 and 10 illustrate three techniques used in solving the noisy test site problem. FIG. 9 plots measured force and acceleration signal levels on processed gravel at a very quiet test site, using a linear frequency sweep. While the force gauge's signal lies well above its noise floor, the accelerometer's signal falls below the preamp broadband noise at about 40 Hz. In addition, a weak hum line at 60 Hz is seen to be about 10 dB above the signal. These measurements were conducted using a commercially available impedance head rather than the preferred instrumentation package illustrated in FIG. 1.

FIG. 10 shows the estimated improvements, first due to substituting a geophone, for the accelerometer used in the commercial impedance head, and then changing the linear sweep to a 20 dB/decade logarithmic sweep, in the 40–400 Hz band (dashed line) That is, the logarithmetric frequency sweep spends 10 times as much time in the 40 Hz frequency bin as did the linear sweep; and one-tenth as much time in the 400 Hz bin. In addition, the preamp noise for the low electrical impedance geophone is lower than the preamp noise for the high impedance accelerometer in the commercial head.

While the first two techniques solve the weak 60 Hz noise problem, it is clear that much stronger lines (e.g. typical compactor lines in the low frequency range) could be removed by deleting narrow bands from the data. The amount of additional noise reduction provided by a tracking filter will depend on the filter's bandwidth. For example, if the filter is designed to have a constant proportional bandwidth, i.e. a constant Q, then the additional noise reduction should be independent of frequency. For example, a further noise reduction of between 10 and 15 dB is expected for a Q of 10, a significant advantage.

Figure 11:
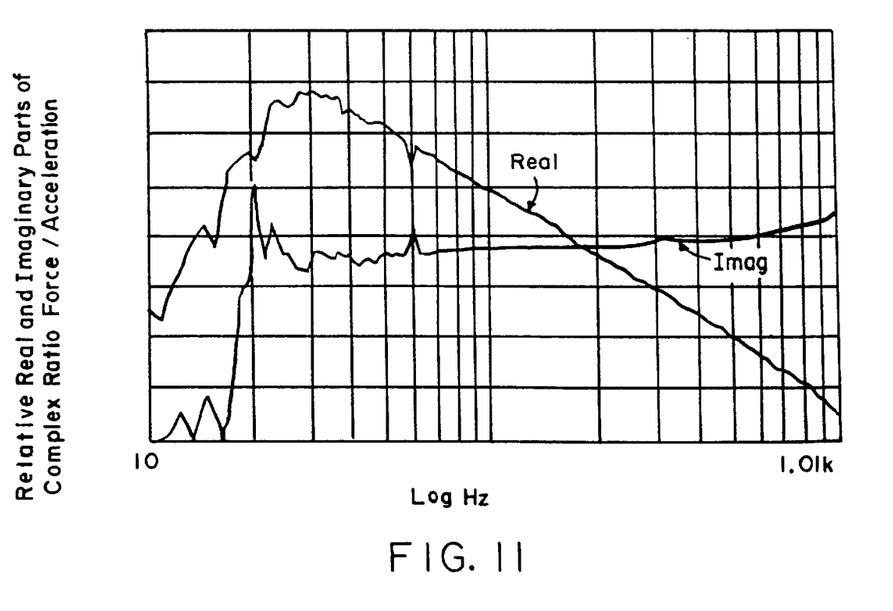
FIG. 11 plots the real and imaginary parts of the complex ratio of the applied force and resulting acceleration signals for FIG. 9.
Figure 12:
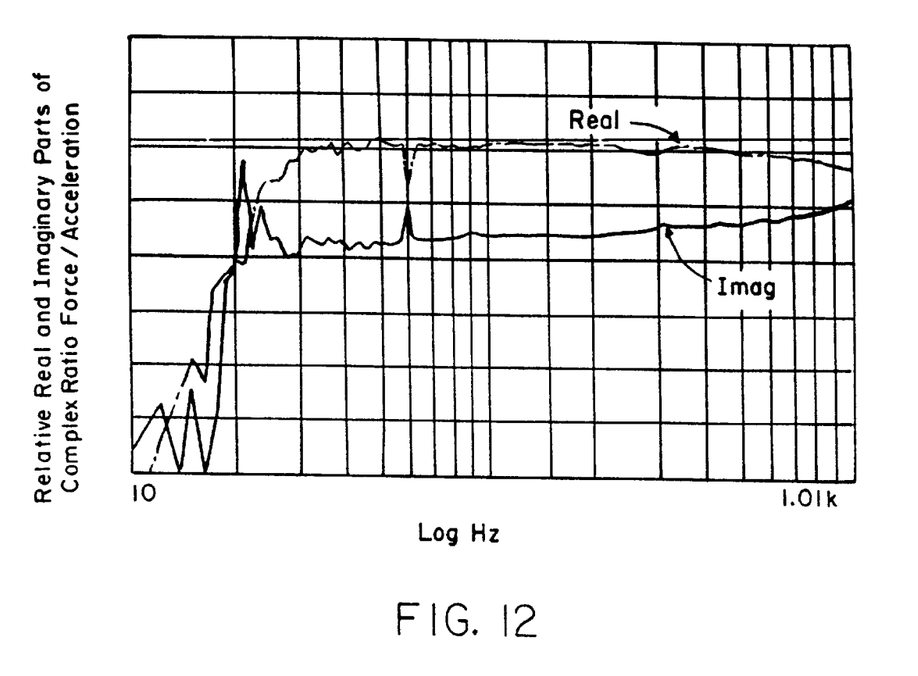
FIG. 12 plots the corresponding real and imaginary parts of the complex ratio of the applied force and the resulting displacement signals.

FIG. 11 plots the complex ratio of the force and accelerometer signals, whose power spectra are shown in FIGS. 9 and 10. The plot of the real part (commonly known as a spring line) is seen to be nearly straight. This is shown more clearly in FIG. 12, where the data of FIG. 11 have multiplied by $j\omega^2$. The average of the real part of the stiffness, in the 40 to 400 Hz frequency band is about 90,000 lbs/in.

The analytical relationship between the shear modulus of an ideal half space and the normal mechanical stiffness seen by a rigid circular disk rigidly attached to the surface of the half space is $$K = \frac{4 \cdot G \cdot a}{(1 - v)}$$

where
K is the stiffness (e.g. in lbs/in)
G is the shear modulus (e.g. in lbs/in$^2$,
a is the radius of the disk (e.g. in inches)
v is Poisson's Ratio The result for the rigid annular foot has been found to be very nearly the same as for a rigid circular disk.

Solving for the effective shear modulus of the soil, assuming that v=¼, yields G=7,600 psi.

The corresponding value of dry density can be estimated from the measured soil stiffness, by using an empirical relationship derived from a large set of field measurements. The mechanical stiffness at each test site was determined using the apparatus of FIG. 1; the dry density was then measured by the sand cone technique. Six different soil types were included in this sampling. The estimated dry density of the soil which produced FIG. 12 was about 124 lbs/cu ft.

Figure 4:
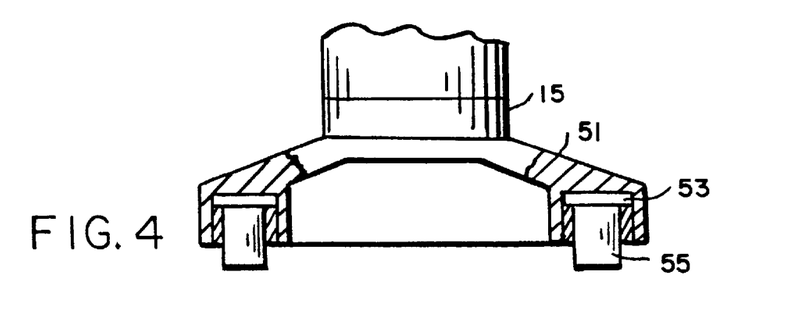
FIG. 4 is a cross-sectional view illustrating an alternate contact foot design.
Figure 5:
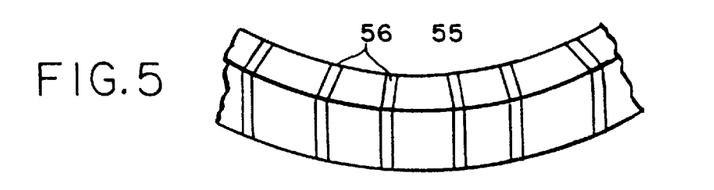
FIG. 5 illustrates a segmented rim employed in the FIG. 4 foot design.

An alternate construction for contacting the soil in the surface area under the contact foot is illustrated in FIGS. 4 and 5. The concept for the annular foot in FIG. 4 is essentially the same as for the annular foot of FIG. 2, except that the articulated design allows the annular foot to conform to a soil surface which is not flat. In this construction, the foot housing 51 provides an annular groove 53. Fitting into the groove 53 are a series of thin metal segments 55 coupled together by a high glass transition temperature viscoelastic material such as plasticized polyvinyl acetate or a urethane such as PRC's 1564, whose modulus decreases drastically at frequencies below about 100 Hz. Such a material, designated by reference character 56 forms a structure which is statically soft so as to conform with soil surface irregularity, but is dynamically rigid so as to transmit vibratory energy. An alternate design to achieve the same result over a wide temperature range would make use of a low durometer low glass transition temperature elastomer such as a silicone rubber for element 56, whose modulus would remain low over a wide temperature range, and thus permit the individual segments to slowly conform to the soil surface irregularity. Dynamic rigidity would be achieved by segmenting volume 53 and then filling it with a fluid such as silicone oil. The individual volumes would be coupled together with small orifices.

Figure 6:
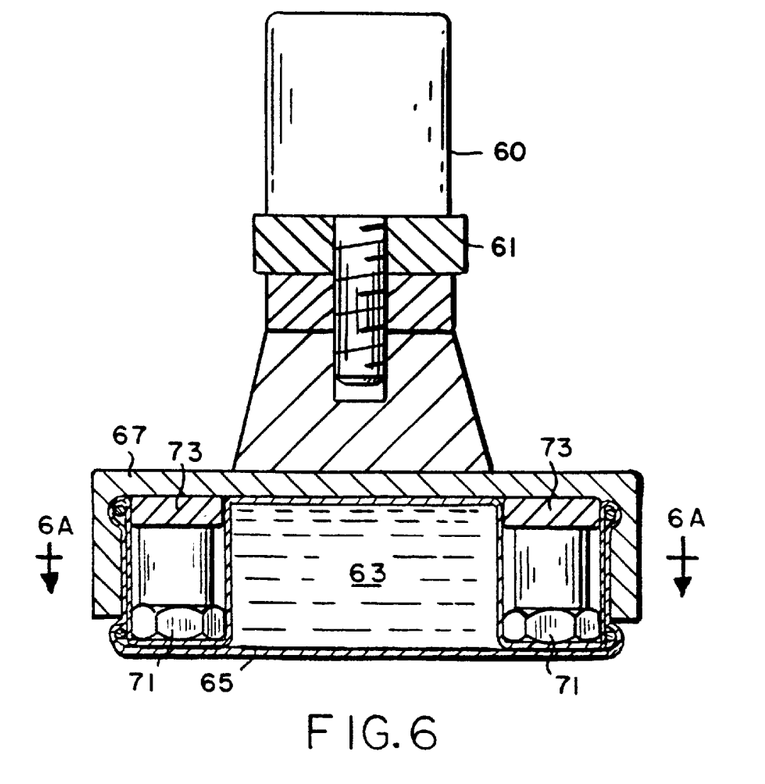
FIG. 6 is a diagram illustrating an alternative construction of contact foot and sensing transducers.
Figure 6A:
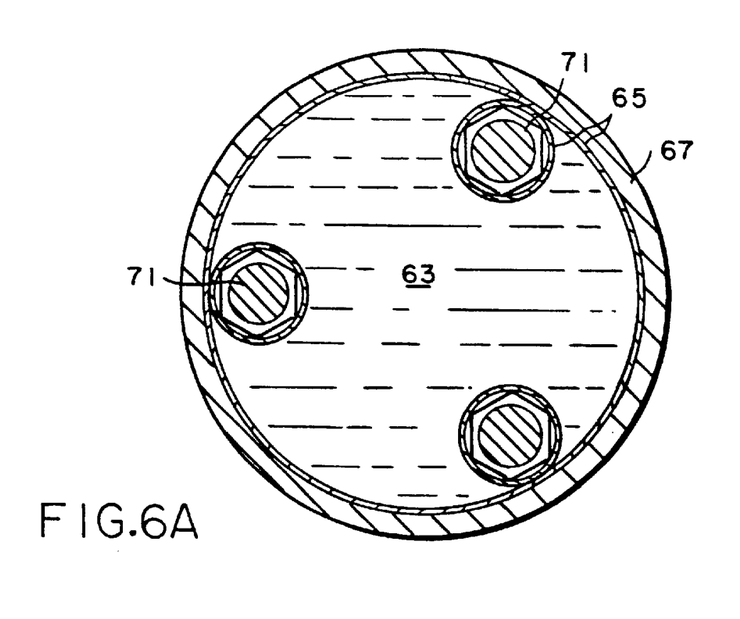
FIG. 6A is a sectional view taken substantially on the line A—A of FIG. 6.

In the embodiment illustrated in FIGS. 6 and 6A, the output of the shaker motor or transducer 60 is coupled to the soil through a force gauge 61 and an oil filled cavity 63 which is defined between top and bottom membranes of a flexible bladder 65 set into a cup-shaped foot 67. The bladder 65 includes a series of pockets, separate from the cavity 63, into which are placed a series (3) of accelerometers 71. Foam spacers 73 isolate the accelerometers from the vibratory motion of the foot so that they instead measure the motion of the soil.

Advantages of this design are the that the lower flexible membrane would apply normal stress to a larger area than would the foot of FIG. 2 or of FIG. 4, and that the membrane should conform to an irregular soil surface much better than would the foot of FIG. 2, and even better than the foot of FIG. 4.

While the bladder is susceptible to puncture, this is dealt with by the fact that three geophones are in contact with the soil's motion without actually being inside the bladder. Likewise, dynamic pressure inside the rubber bag is sensed from outside the bag by the force gauge 61 shown in FIG. 6. Thus, an inadvertent cut in the membrane could quickly be remedied by snapping a spare bladder into place.

Figure 7:
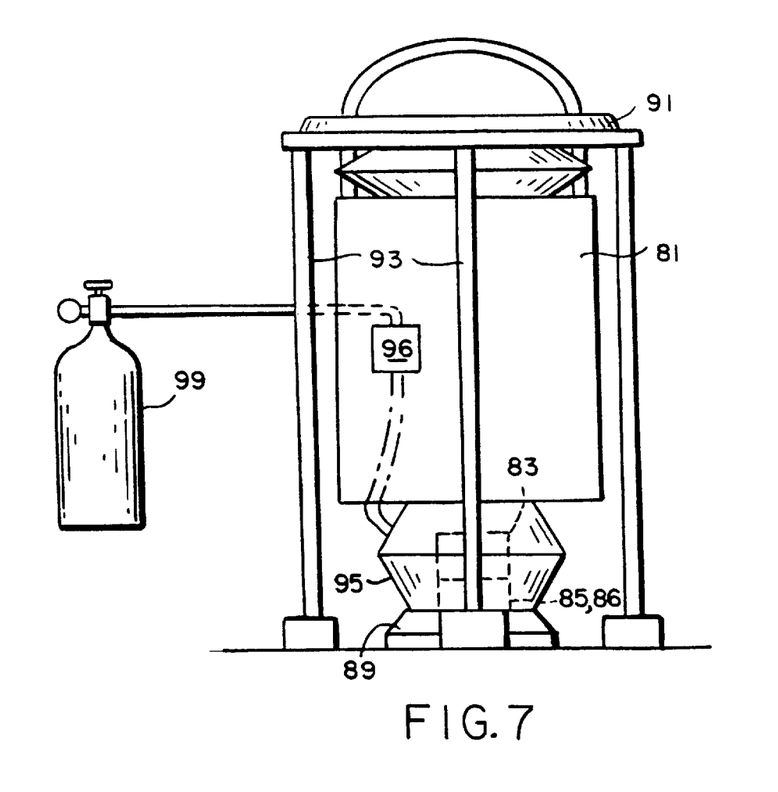
FIG. 7 is a side view of alternate construction of the measurement apparatus providing for automatic variation of bias force.

It is well known that the modulus of soils depends on the effective static stress. The weight of the devices shown in FIG. 1 and FIG. 2 would be chosen to produce a known, typical stress in the soil beneath the foot (reference character 11). To further improve accuracy of measurement, multiple scans of varying frequency excitation may be performed at different levels of downward bias force, i.e. overburden. It is advantageous that the change in bias force be provided automatically. In the embodiment illustrated in FIG. 7, a housing 81 contains the batteries and electronics, separate from the shaker motor 83 and the sensing transducers 85 and 86 which are coupled to the contact foot 89. Coupled to the housing 81 is a frame 91 having a plurality of feet 93 which contact the ground at spaced locations around the contact foot 89. An air spring 95 selectively couples downward force from the housing 81 to the contact foot 89 in accordance with the pressure within the air spring. A tank 99 of compressed air provides a source of air for selectively pressurizing the air spring. Solenoid valves 96, operated under the control of the programmable digital processor incorporated in the electronics package, are provided for selectively venting or filling the air spring. As an alternative, weights could be manually added in a preselected progression to an instrument package such as that illustrated in FIG. 1.

In view of the foregoing it may be seen that several objects of the present invention are achieved and other advantageous results have been attained.

As various changes could be made in the above constructions without departing from the scope of the invention, it should be understood that all matter contained in the above description or shown in the accompanying drawings shall be interpreted as illustrative and not in a limiting sense.

What is claimed is:

1. Man portable apparatus for the in-situ measurement of the shear modulus of a compacted layer of soil, said apparatus comprising:

a contact foot for engaging a region of soil in the order of 4½ inches in nominal diameter;

means for applying a downwardly biasing force to said foot, said force being in the order of 35 pounds;

means for generating an a.c. drive signal;

a drive transducer responsive to said drive signal for applying a vibratory vertical force to said contact foot;

a first sensing transducer for sensing motion of said foot and generating a corresponding first output signal;

means including a second sensing transducer for sensing force applied to said foot and generating a corresponding second output signal;

circuit means for measuring a component of said first output signal which is in phase with said second output signal thereby to obtain a value for a single parameter which is representative of the shear modulus.

2. Apparatus as set forth in claim 1 wherein said a.c. drive signal progressively varies in frequency over a preselected band at a rate of change of frequency, which also varies with frequency so that, for constant amplitude, energy content varies with frequency.

3. Man portable apparatus for the in-situ measurement of the shear modulus of a compacted layer of soil, said apparatus comprising:

a contact foot for engaging a region of soil corresponding to said compacted layer;

means for applying a downwardly biasing force to said foot;

a calibrated spring one end of which is connected to said contact foot;

means for generating an a.c. drive signal;

a drive transducer responsive to said drive signal for vibrating another end of said spring thereby to apply a vibratory vertical force to said contact foot;

a first sensing transducer for sensing motion of said foot and generating a corresponding first output signal;

means including a second sensing transducer for sensing motion of said other end of said spring and generating a corresponding second output signal;

circuit means for measuring a component of said first output signal which is in phase with said second output signal thereby to obtain a value for a single parameter which is representative of the shear modulus.

4. Apparatus as set forth in claim 3 wherein said contact foot has a nominal diameter in the order of 4½ inches.

5. Apparatus as set for in claim 3 wherein said downwardly biasing force is in the order of 35 pounds.

6. Man portable apparatus for the in-situ measurement of the shear modulus of a compacted layer of soil, said apparatus comprising:

a contact foot for engaging a region of soil in the order of 4½ inches in nominal diameter;

means for applying a downwardly biasing force to said foot, said force being in the order of 35 pounds;

a calibrated spring one end of which is connected to said contact foot;

means for generating an a.c. drive signal;

a drive transducer responsive to said drive signal for vibrating another end of said spring thereby to apply a vibratory vertical force to said contact foot;

a first sensing transducer for sensing motion of said foot and generating a corresponding first output signal;

means including a second sensing transducer for sensing motion of said other end of said spring and generating a corresponding second output signal;

circuit means for measuring the component of said first output signal which is in phase with said second output signal thereby to obtain a value for a single parameter which is representative of the shear modulus.

7. Apparatus as set forth in claim 6 wherein said sensing transducers are geophones.

8. Apparatus as set forth in claim 6 wherein said sensing transducers are moving coil velocity sensors.

9. Apparatus as set forth in claim 8 wherein said drive transducer and said second sensing transducer are connected to said foot through a spring and wherein said first output signal is obtained by integration of a first sensor signal obtained from said first sensing transducer and wherein said second output signal is obtained as a function of the difference between the integral of the first sensor signal and the integral of a second sensor signal obtained from the second sensing transducer.

10. Apparatus as set forth in claim 6 wherein said foot has a downwardly projecting annular rim for confining the soil in said surface area.

11. Apparatus as set forth in claim 10 wherein said annular rim is rigid and continuous and has a roughened lower surface.

12. Apparatus as set forth in claim 10 wherein said annular rim comprises a series of rigid segments joined by a low glass-temperature viscoelastic material.

13. Apparatus as set forth in claim 6 further comprising means for applying a progressively varying downward bias force to said foot, for repeatedly initiating successive sweeps of a frequency of the a.c. drive signal, and for analyzing the resulting first and second output signals at different levels of the downward bias force.

14. Apparatus for the in-situ measurement of the shear modulus of soil, said apparatus comprising:
   a contact foot for engaging a defined surface area of a region of soil to be measured;
   a drive transducer for shaking said contact foot vertically in response to drive signals applied to the transducer;
   a first sensing transducer for sensing the motion acceleration of said foot and generating a corresponding first output signal;
   means including a second sensing transducer for determining the force applied to said foot and generating a corresponding second output signal;
   means for applying to said drive transducer an a.c. drive signal which progressively varies in frequency over a preselected band at a rate of change of frequency, which also varies with frequency so that, for constant amplitude, energy content varies with frequency;
   circuit means for analyzing said first output signal in relation to said second output signal to obtain a measurement of an in-phase component of said first output signal which then is representative of the shear modulus.

15. Apparatus as set forth in claim 14 wherein said contact foot has a nominal diameter in the order of 4½ inches.

16. Apparatus as set for in claim 14 wherein said apparatus has a weight, which applies a downwardly biasing force to the contact foot in the order of 35 pounds.

17. Apparatus as set forth in claim 14 wherein said sensing transducers are geophones.

18. Apparatus as set forth in claim 14 wherein said sensing transducers are moving coil velocity sensors.

19. Apparatus as set forth in claim 18 wherein said drive transducer and said second sensing transducer are connected to said foot through a spring and wherein said first output signal is obtained by integration of a first sensor signal obtained from said first sensing transducer and wherein said second output signal is obtained as a function of the difference between the integral of the first sensor signal and the integral of a second sensor signal obtained from the second sensing transducer.

20. Apparatus as set forth in claim 14 wherein said foot has a downwardly projecting annular rim for confining the soil in said surface area.

21. Apparatus for the in-situ measurement of the shear modulus of soil, said apparatus comprising:
   a contact foot for engaging a defined surface area of a region of soil to be measured, said foot including a rigid top portion and a lower, flexible membrane portion, the space between said membrane portion and said top portion being filled with an essentially incompressible liquid for coupling force to said region of soil;
   a drive transducer for shaking said contact foot in response to drive signals applied to the transducer;
   a first sensing transducer for sensing the force applied to said foot and generating a corresponding first output signal;
   a second sensing transducer for sensing the acceleration of soil under said lower membrane portion and for generating a corresponding second output signal;
   means for applying to said drive transducer an a.c. drive signal which progressively varies in frequency over a preselected band;
   circuit means for analyzing said second output signal in relation to said first output signal to obtain a measurement which represents the desired shear modulus.

* * * * *